United States Patent [19]
Wei et al.

[11] Patent Number: 5,858,705
[45] Date of Patent: Jan. 12, 1999

[54] POLYNUCLEOTIDES ENCODING HUMAN DNA LIGASE III AND METHODS OF USING THESE POLYNUCLEOTIDES

[75] Inventors: Ying-Fei Wei; Guo-Liang Yu, both of Darnestown, Md.; William A. Haseltine, Washington, D.C.

[73] Assignee: Human Genome Sciences, Inc., Rockville, Md.

[21] Appl. No.: 464,402

[22] Filed: Jun. 5, 1995

Related U.S. Application Data

[63] Continuation-in-part of PCT/US95/03939 Mar. 31, 1995.
[51] Int. Cl.$^6$ .............................. C12N 15/52; C12N 15/63
[52] U.S. Cl. ................ 435/69.1; 435/252.3; 435/254.11; 435/320.1; 435/325; 435/183; 536/23.2
[58] Field of Search .......................... 536/23.2; 435/69.1, 435/172.3, 252.3, 254.11, 320.1, 325, 183

[56] References Cited

FOREIGN PATENT DOCUMENTS

90/12101  10/1990  WIPO .

OTHER PUBLICATIONS

Tomkinson et al. DNA ligase III is the major high molecular weight DNA joining activity in SV40–transformed human fibroblasts: normal levels of DNA ligase III activity in Bloom syndrome cells. Nucleic Acids Research. vol. 21, No. 23, pp. 5425–5430, Nov. 25, 1993.

Caldecott et al. An interaction between the mammalian DNA repair protein XRCC1 and DNA ligase III. Molecular and Cellular Biology. vol. 14, pp. 68–76, Jan. 1994.

Tomkinson et al. Three distinct DNA ligases in mammalian cells. The Journal of Biological Chemistry. vol. 266, No. 32, pp. 21728–21735, Nov. 15, 1991.

Auffray et al. Partial cDNA sequence in EST–STS database, Accession No. Z45685, Nov. 6, 1994.

Auffray et al. Partial cDNA sequence in EST–STS database, Accession No. T95824, Mar. 27, 1995.

Auffray et al. Partial cDNA sequence in EST–STS database, Accession No. D15404, Mar. 18, 1995.

Auffray et al. Partial cDNA sequence in EST–STS database, Accession No. F07530, Feb. 17, 1995.

Auffray et al. Partial cDNA sequence in STS–EST database, Accession No. F00233, Mar. 7, 1995.

Hillier et al. Partial cDNA sequence in STS–EST database, Accession No. T95919, Mar. 27, 1995.

Clark et al. Beta–centractin: characterization and distribution of a new member of the centractin family of actin–related proteins. Molecular Biology of the Cell. vol. 5, No. 12, pp. 1301–1310, Dec. 1994.

*Primary Examiner*—Stephen Walsh
*Assistant Examiner*—Brian Lathrop
*Attorney, Agent, or Firm*—Elliot M. Olstein; J. G. Mullins

[57] ABSTRACT

A human DNA Ligase III polypeptide and DNA (RNA) encoding such polypeptide and a procedure for producing such polypeptide by recombinant techniques are disclosed. Also disclosed are methods for utilizing such polypeptide via gene therapy for the treatment of disorders associated with a defect in DNA Ligase III. Antagonists against such polypeptides and their use as a therapeutic to destroy unwanted cells are also disclosed. Diagnostic assays to detect mutant DNA Ligase III genes are also disclosed.

19 Claims, 12 Drawing Sheets

FIG. 1A

```
-330            -310                            -290
  .               .                               .
CCACGGCGTTCCGGCAGCCTGTATGAGCAAGTGCCGGAGGCCTACGGTGAGGCGCCGGAGCCGG
--+---------+---------+---------+---------+---------+---------+--
GGTGCGCAGGCCGTCGGACATACTCGTTCACGGCTCCGGATGCCACTCGCGGCCTCGGCC
        -270                            -250                 -230
                .                         .                    .
AGAGGCAGCTATATGTCTTTGGCTTTCAAGATCTTCTTCCACAAACCCTCCGTGCACTC
--+---------+---------+---------+---------+---------+---------+--
TCTCCGTCGATATACAGAAACCGAAACTTCTTAGAAGAAAGGTGTTTGGGAGGCACGTGAG
  -210                           -190                          -170
             .                         .                         .
AGCCGAAAAGAACTGTGCCTATTCCGAAAAACATCACTGGCGTGATGTAAGACAATTCAGC
--+---------+---------+---------+---------+---------+---------+--
TCGGCTTTTCTTGACACGGATAAGGCTTTTGTAGTGACCGCACTACATTCTGTTAAGTCG
150                            -130                           -110
              .                         .                         .
CAGTGGTCAGAAACAGATCTGCTTCATGGACATCCCCTCTCCTGAGAAGAAAGCCTGTT
--+---------+---------+---------+---------+---------+---------+--
GTCACCAGTCTTTGTCTAGACGAAGTACCTGTAGGGGAGAAGGACTCTTCTTTCGGACAA
     -90                             -70                          -50
             .                         .                         .
CTATCATTCCAGGGAAGCCATCTAAGATCACGTGCCACCTACCTTGTTTTCTTGCCAGGG
--+---------+---------+---------+---------+---------+---------+--
GATAGTAAGGTCCCTTCGGTAGATTCTAGTGCACGGTGGATGGAACAAAGAACGGTCCC
          -30                            -10                         10
                 .                         .
TTGCATGTGGGACTCTGCAGTGGCCCCTGTGAGATGGCTGAGCAACGGTTCTGTGTGGAC
```

FIG. 1B

```
         --+---------+---------+---------+---------+---------+---------
           AACGTACACCCTGAGACGTCACCGGGACACTCTACCGACTCGTTGCCAAGACACACCTG
                                            M  A  E  Q  R  F  C  V  D
              30                  50                  70

TATGCCAAGCGTGGCACAGCTGGCTGCAAAAATGCAAGGAAAAGATTGTGAAGGGCGTA
         --+---------+---------+---------+---------+---------+---------
           ATACGGTTCGCACCGTGTCGACCGACTGTTTTACGTTCCTTTTCTAACACTTCCCGCAT
            Y  A  K  R  G  T  A  G  C  K  K  C  K  E  K  I  V  K  G  V
                   90                 110                 130

TGCCGAATTGGCAAAGTGGTCGTGCCCAATCCCTTCTCAGAGTCTGGGGTGATATGAAAGAG
         --+---------+---------+---------+---------+---------+---------
           ACGGCTTAACCGTTTCACCAGCACGGGTTAGGGAAGAGTCTCAGACCCCACTATACTTTCTC
            C  R  I  G  K  V  V  P  N  P  F  S  E  S  G  G  D  M  K  E
                  150                 170                 190

TGGTACCACATTAAATGCATGTTTGAGAAACTAGAGCGGCCCCGGCCACCACAAAAAAA
         --+---------+---------+---------+---------+---------+---------
           ACCATGGTGTAATTTACGTACAAACTCTTTGATCTCGCCGGGGCCGGTGGTGTTTTTTT
            W  Y  H  I  K  C  M  F  E  K  L  E  R  A  R  A  T  T  K  K
                  210                 230                 250

ATCGAGGACCTCACAGAGCTGGAAGGCTGGGAAGAGCTGGAAGATAATGAGAAGGAACAG
         --+---------+---------+---------+---------+---------+---------
           TAGCTCCTGGAGTGTCTCGACCTTCCGACCCTTCTCGACCTTCTATTACTCTTCCTTGTC
            I  E  D  L  T  E  L  E  G  W  E  E  L  E  D  N  E  K  E  Q
                  270                 290                 310
```

FIG. 1C

```
ATAACCCAGCACATTGCAGATCTGTCTCTTCTAAGGCAGCAGTACACCAAAGAAGAAAGCT
--!----!----!----!----!----!----!----!----!----!----!----!--
TATTGGGTCGTGTAACGTCTAGACAGAAGATTCCGTCGTCCATGTGGTTTCTTCTTTCGA
 I  T  Q  H  I  A  D  L  S  S  K  A  A  G  T  P  K  K  K  A
330                      350                      370

GTTGTCCAGGCTAAGTTGACAACCACTGGCCAGTGACTTCTCCAGTGAAAGGCGCCCTCA
--!----!----!----!----!----!----!----!----!----!----!----!--
CAACAGGTCCGATTCAACTGTTGGTGACCGGTCACTGAAGAGGTCACTTTCCGCGGGAGT
 V  V  Q  A  K  L  T  T  T  G  Q  V  T  S  P  V  K  G  A  S
390                      410                      430

TTTGTCACCAGTACCAATCCCCGGAAATTTTCTGGCTTTTCAGCCAAGCCCAACAACTCT
--!----!----!----!----!----!----!----!----!----!----!----!--
AAACAGTGGTCATGGTTAGGGCCTTTAAAAGACCGAAAAGTCGGTTCGGGTTGTTGAGA
 F  V  T  S  T  N  P  R  K  F  S  G  F  S  A  K  P  N  N  S
450                      470                      490

GGGGAAGCCCCCTCGAGCCCCACCCCTAAGAGAAGTCTGTCTTCAAGCAAATGTGACCCC
--!----!----!----!----!----!----!----!----!----!----!----!--
CCCCTTCGGGGGAGCTCGGGGTGGGGATTCTCTTCAGACAGAAGTTCGTTTACACTGGGG
 G  E  A  P  S  S  P  T  P  K  R  S  L  S  S  S  K  C  D  P
510                      530                      550

AGGCATAAGGACTGTCTGCTACGGGAGTTTCGAAAGTTATGCGCCATGGTGGCCGATAAT
--!----!----!----!----!----!----!----!----!----!----!----!--
```

FIG. 1D

```
TCCGTATTCCTGACAGACGATGCCCTCAAAGCTTTCAATACGGGTACCACCGGCTATTA
R  H  K  D  C  L  L  R  E  F  R  K  L  C  A  M  V  A  D  N
      570                     590                    610

CCTAGCTACAACACGAAGACCCAGATCATCCAGGACTTCCTTCGGAAAGGCTCAGCAGGA
P  S  Y  N  T  K  T  Q  I  I  Q  D  F  L  R  K  G  S  A  G
      630                     650                    670

GGATCGATGTTGTGCTTCTGGGTCTAGTAGTCCTGAAGGAAGCCTTTCGAGTCGTCCT
D  G  F  H  G  D  V  Y  L  T  V  K  L  L  P  G  V  I  K
      690                     710                    730

GATGGTTTCCACGGTGATGTGTACCTAACAGTGAAGCTGCTGCCAGGAGTCATTAAG

CTACCAAAGTGCCACTACACAGATTGTCACTTCGACGACGGTCCTCAGTAATTC

ACTGTTTACAACTTGAACGATAAGCAGATTGTGAAGCTTTTCAGTCGCATTTTTAACTGC
T  V  Y  N  L  N  D  K  Q  I  V  K  L  F  S  R  I  F  N  C
      750                     770                    790

AACCCAGATGATATGGCACGGGACCTAGAGCAGGGTGACGTGTCAGAGACAATCAGAGTC
N  P  D  D  M  A  R  D  L  E  Q  G  D  V  S  E  T  I  R  V
      810                     830                    850

TGAACAAATGTTGAACTTGCTATTCGTCTAACACTTGAAAAGTCAGGTAAAAATTGACG

TTGGGTCTACTATACCGTGCCCTGGATCTCGTCCCACTGCACAGTCTCTGTTAGTCTCAG
```

FIG. 1E

```
TTCTTTGAGCAGAGCAAGTCTTCCCCCCAGCTGCCAAGAGCCTCCTTACCATCCAGGAA
--+---------+---------+---------+---------+---------+---------+--
AAGAAACTCGTCTCGTTCAGAAGGGGGGTCGACGGTTCTCGGAGGAATGGTAGTCCTT
 F  F  E  Q  S  K  S  F  P  P  A  A  K  S  L  L  T  I  Q  E
                    890                             910

GTGGATGAGTTCCTTCTGCGGCTGTCCAAGCTCACCAAGGAGGATGAGCAGCAACAGGCC
--+---------+---------+---------+---------+---------+---------+--
CACCTACTCAAGGAAGACGCCGACAGGTTCGAGTGGTTCCTCCTACTCGTCGTTGTCCGG
 V  D  E  F  L  L  R  L  S  K  L  T  K  E  D  E  Q  Q  Q  A
                    930                             950                             970

CTACAGGACATTGCCTCCAGGTGTACAGCCAATGACCTTAAATGCATCATCAGGTTGATC
--+---------+---------+---------+---------+---------+---------+--
GATGTCCTGTAACGGAGGTCCACATGTCGGTTACTGGAATTTACGTAGTAGTCCAACTAG
 L  Q  D  I  A  S  R  C  T  A  N  D  L  K  C  I  I  R  L  I
               990                            1010                            1030

AAACATGATCTGAAGATGAACTCAGGTGCAAAACATGTGTTAGACGCCCTTGACCCCAAT
--+---------+---------+---------+---------+---------+---------+--
TTTGTACTAGACTTCTACTTGAGTCCACGTTTTGTACACAATCTGCGGGAACTGGGGTTA
 K  H  D  L  K  M  N  S  G  A  K  H  V  L  D  A  L  D  P  N
                   1050                            1070                            1090

GCCTATGAAGCCTTCAAAGCTTGCGCAACCTGCAGGATGTGGAGCGGGTCCTTCAC
--+---------+---------+---------+---------+---------+---------+--
CGGATACTTCGGAAGTTTCGGAGCGCGTTGGACGTCCTACACCACCTCGCCCAGGAAGTG
 A  Y  E  A  F  K  A  S  R  N  L  Q  D  V  V  E  R  V  L  H
```

FIG. 1F

```
                   1130                        1150
       1110           .                           .
         .            .                           .
AACGCGCAGGAGGTGGAGAAGGAGCCGGGGCCAGAGACGAGCTCTGAGCGTCCAGGCCTCG
-+---------+---------+---------+---------+---------+---------+
TTGCGCGTCCTCCACCTCTTCCTCGGCCCGGGTCTCTGTCTCGAGACTCGCAGGTCCGAGC
 N  A  Q  E  V  E  K  E  P  G  Q  R  R  A  L  S  V  Q  A  S
170                          1190                       1210

CTGATGACACCTGTGCAGCCCATGTTGGCGGAGGCCTGCAAGTCCGTTGAGTATGCAATG
-+---------+---------+---------+---------+---------+---------+
GACTACTGTGGACACGTCGGGTACAACCGCTCCGGACGTTCAGGCAACTCATACGTTAC
 L  M  T  P  V  Q  P  M  L  A  E  A  C  K  S  V  E  Y  A  M
            1230                       1250                       1270

AAGAAATGTCCCAATGGCATGTTCTCTGAGATCAAGTACGATGGAGAGCGAGTCCAGGTG
-+---------+---------+---------+---------+---------+---------+
TTCTTTACAGGGTTACCGTACAAGAGACTCTAGTTCATGCTACCTCTCGCTCAGTCCAC
 K  K  C  P  N  G  M  F  S  E  I  K  Y  D  G  E  R  V  Q  V
           1290                       1310        ↑              1330

CATAAGAATGGAGACCACTTCAGCTACTTCAGCCGCAGTCTCAAGCCCGTCCTTCCTCAC
-+---------+---------+---------+---------+---------+---------+
GTATTCTTACCTCTGGTGAAGTCGATGAAGTCGGCGTCAGAGTTCGGCAGGAAGGAGTG
 H  K  N  G  D  H  F  S  Y  F  S  R  S  L  K  P  V  L  P  H
          1350                       1370                       1390

AAGGTGGCCCACTTTAAGGACTACATTCCCCAGGCTTTTCCTGGGGGCCACAGCATGATC
-+---------+---------+---------+---------+---------+---------+
```

FIG. 1G

```
TTCCACCGGGTGAAATTCCTGATGTAAGGGTCCGAAAGGACCCCCGGTGTCGTACTAG
K  V  A  H  F  K  D  Y  I  P  Q  A  F  P  G  G  H  S  M  I
1410                      1430                      1450

TTGGATTCTGAAGTGCTTCTGATTGACAACAGACAGGCAAACCACTGCCCTTGGGACT
AACCTAAGACTTCACGAAGACTAACTGTTGTTGTCCGTTGGTGACGGGAACCCTGA
L  D  S  E  V  L  L  I  D  N  K  T  G  K  P  L  P  F  G  T
1470                      1490                      1510

CTGGGAGTACACAAGAAAGCAGCCTTCCAGGATGCTAATGTCGCCTGTTTGTTTTTGAT
GACCCTCATGTGTTCTTTCGTCGGAAGGTCCTACGATTACAGACGGACAACAAAAACTA
L  G  V  H  K  K  A  A  F  Q  D  A  N  V  C  L  F  V  F  D
1530                      1550                      1570

TGTATCTACTTTAATGATGTCAGCTTGATGGACAGACCTCTGTGTGAGCGGCGGAAGTTT
ACATAGATGAAATTACTACAGTCGAACTACCTGTCTGGAGACACACTCGCCGCCTTCAAA
C  I  Y  F  N  D  V  S  L  M  D  R  P  L  C  E  R  R  K  F
1590                      1610                      1630

CTTCATGACAACATGGTTGAAATTCCAAACCGGATCATGTTCTCAGAAATGAAGCGAGTC
GAAGTACTGTTGTACCAACTTTAAGGTTTGGCCTAGTACAAGAGTCTTTACTTCGCTCAG
L  H  D  N  M  V  E  I  P  N  R  I  M  F  S  E  M  K  R  V
1650                      1670                      1690

ACAAAGCTTTGGACTTGGCTGACATGATAACCCGGGTGATCCAGGAGGGATTGGAGGGG
```

FIG. 1H

```
TGTTTCGAAACCTGAACCGACTGTACTATTGGGCCACTAGTCCTCCCTAACCTCCCC
 T   K   A   L   D   L   A   D   M   I   T   R   V   I   Q   E   G   L   E   G
                        1710                             1730                             1750

CTGGTGCTGAAGGATGTGAAGGTACATATGAGCCTGGAAGCGGCACTGGCTGAAAGTG
 L   V   L   K   D   V   K   G   T   Y   E   P   G   K   R   H   W   L   K   V
        1770                             1790                             1810

GACCACGACTTCCTACACTTCCCATGTATACTCGGACCCTTCGCCGTGACCGACTTCAC

AAGAAAGACTATTTGAACGAGGGGCCATGGCCGACACAGCTGACCTGGTGGTCCTTGGA
 K   K   D   Y   L   N   E   G   A   M   A   D   T   A   D   L   V   V   L   G
        1830                             1850                             1870

TTCTTTCTGATAAACTTGCTCCCCCGGTACCGGCTGTGTCGACTGGACCACCAGGAACCT

GCCTTCTATGGGCAAGGGAGCAAAGGCGGCATGATGTCAATCTTCCTCATGGGCTGCTAC
 A   F   Y   G   Q   G   S   K   G   G   M   M   S   I   F   L   M   G   C   Y
        1890                             1910                             1930

CGGAAGATACCCGTTCCCTCGTTCCGCCGTTAGAAGGAGTACCCGACGATG

GACCCTGGCAGCCAGAAGTGGTGCACAGTCACCAAGTGTGCAGGAGGCCATGATGATGCC
 D   P   G   S   Q   K   W   C   T   V   T   K   C   A   G   G   H   D   D   A
        1950                             1970                             1990

CTGGACCGTCGTCTTCACCACGTGTCAGTGGTTCACACGTCCTCCGGTACTACTACGG
```

FIG. 1I

```
ACGCTTGCCCGCCTGCAGAATGAACTAGACATGGTGAAGATCAGCAAGGACCCCAGCAAA
---+---------+---------+---------+---------+---------+
TGCGAACGGGCGGACGTCTTACTTGATCTGTACCACTTCTAGTCGTTCCTGGGGTCGTTT
 T  L  A  R  L  Q  N  E  L  D  M  V  K  I  S  K  D  P  S  K
 2010                          2030                       2050

ATACCCAGCTGTTGAAGTCAACAAGATCTACTATCCTGACTTCATCGTCCCAGACCA
---+---------+---------+---------+---------+---------+
TATGGGTCGACCAACTTCCAGTTGTTCTAGATGATAGGACTGAAGTAGCAGGTCTGGT
 I  P  S  W  L  K  V  N  K  I  Y  Y  P  D  F  I  V  P  D  P
 2070                          2090                      2110

AAGAAAGCTGCCGTGTGGGAGATCACAGGGGCTGAATTCTCCAAATCGGAGGCTCATACA
---+---------+---------+---------+---------+---------+
TTCTTTCGACGGCACACCCTCTAGTGTCCCCGACTTAAGAGGTTTAGCCTCCGAGTATGT
 K  K  A  A  V  W  E  I  T  G  A  E  F  S  K  S  E  A  H  T
 2130                          2150                      2170

GCTGACGGGATCTCCATCCGATTCCCTCGCTGCACCCGAATCCGAGATGATAAGGACTGG
---+---------+---------+---------+---------+---------+
CGACTGCCCTAGAGGTAGGCTAAGGGAGCGACGTGGGCTTAGGCTCTACTATTCCTGACC
 A  D  G  I  S  I  R  F  P  R  C  T  R  I  R  D  D  K  D  W
 2190                          2210                      2230

AAATCTGCCACTAACCTTCCCCAACTCAAGGAACTGTACCAGTTGTCCAAGGAGAAGGCA
---+---------+---------+---------+---------+---------+
TTTAGACGGTGATTGGAAGGGGTTGAGTTCCTTGACATGGTCAACAGGTTCCTCTTCCGT
```

FIG. 1J

```
K   S   A   T   N   L   P   Q   L   K   E   L   Y   Q   L   S   K   E   K   A
250                         2270                        2290
    GACTTCACTGTAGTGGCTGGAGATGAGGGAGCTCCACTACAGGGGTAGCAGTGAAGAG
    CTGAAGTGACATCACCGACCTCTACTCCCCTCGAGGTGATGTCCCCATCGTCACTTCTC
D   F   T   V   V   A   G   D   E   G   S   S   T   T   G   G   S   S   E   E
    2310                        2330                        2350
    AATAAGGGTCCCTCAGGTCTGTGTCCCGCAAGGCCCCAGCAAGCCCTCAGCCAGT
    TTATTCCCAGGGAGTCCCAGACACAGGCCGTTCCGGGGTCGTTCGGGAGTCGGTCA
N   K   G   P   S   G   S   A   V   S   R   K   A   P   S   K   P   S   A   S
    2370                        2390                        2410
    ACCAAGAAAGCAGAAGGGAAGCTGAGTAACTCCAACAGCAAAGATGCAACATGCAGACT
    TGGTTCTTTCGTCTTCCCTTCGACTCATTGAGGTTGTCGTTTCTACCGTTGTACGTCTGA
T   K   K   A   E   G   K   L   S   N   S   N   S   K   D   G   N   M   Q   T
    2430                        2450                        2470
    GCAAAGCCTTCCGCTATGAAGGTGGGGAGAAGCTGGCCACAAAGTCTTCTCCAGTGAAA
    CGTTTCGGAAGGCGATACTTCCACCCCCTCTTCGACCGTGTTTCAGAAGAGGTCACTTT
A   K   P   S   A   M   K   V   G   E   K   L   A   T   K   S   S   P   V   K
    2490                        2510                        2530
    GTAGGGGAGAAGCGGAAAGCTGCTGATGAGACGCTGTGCCAAACAAAGGTATTGCTGGAC
```

FIG. 1K

```
CATCCCCCTCTTGCCTTTCGACGACTACTCTGCGACACGGTTTGTTTCCATAACGACCTG
V  G  E  K  R  K  A  A  D  E  T  L  C  Q  T  K  V  L  L  D
            2570                        2590

ATCTTCACTGGGGTGCGGCTTTACTTGCCACCTCCACACCAGACTTCAGCCGTCTCAGA
I  F  T  G  V  R  L  Y  L  P  P  S  T  P  D  F  S  R  L  R
            2610                        2630

TAGAAGTGACCCCACGCCGAAATGAACGGTGGAGGTGTGTCTGAAGTCGGCAGAGTCT
                                                2650

CGCTACTTTGTGGCATTCGACGGGGACCTGGTACAGGAATTTGATATGACTTCAGCCACG
R  Y  F  V  A  F  D  G  D  L  V  Q  E  F  D  M  T  S  A  T
            2670                        2690

GCGATGAAACACCGTAAGCTGCCCCTGGACCATGTCCTAAACTATACTGAAGTCGGTGC
                                                2710

CACGTGCTGGGTAGCAGGGACAAGAACCCTGCGGGCCCAGCAGGTCTCCCCAGAGTGGATT
H  V  L  G  S  R  D  K  N  P  A  A  Q  Q  V  S  P  E  W  I
            2730                        2750                        2770

GTGCACGACCATCGTCCCTGTTCTTGGGACGCGGTCTGCTGCCCAGAGGGTCTCACCTAA

TGGGCATGTATCCGGAAACGGAGACTGGTAGCTCCCTGCTAGGTTTGCTGTCTTCCCTCT

ACCCGTACATAGGCCTTTGCCTCTGACCATCGAGGGACGATCCAAACGACAGAAGGGAGA
W  A  C  I  R  K  R  R  L  V  A  P  C  *
            2790                        2810                        2830

CCCTCAGGCCATACTCTCCTTACCATACTATTGGACTGGACTCAGGCTGGAGGCAGATA
```

FIG. 1L

```
    -+----------+----------+----------+----------+----------+----------
    GGGAGTCCGGTATGAGAGAGGAAATGGTATGATAACCTGAGTCCGACCTCCGTCTAT
            2850                  2870                  2890
         .         .         .         .         .         .
    GACACAGTATAGGGGGAATGGGCTTGCTCTCCCAAACCCACCAGTTCTCCACTGTCT
    ----+----------+----------+----------+----------+----------+-----
    CTGTGTCATATCCCCCTTACCCGAACGAAGAGGGTTTGGGTGGTCAAGAGGTGACAGAGA
            2910                  2930                  2950
         .         .         .         .         .         .
    TCTGGACCAGGAATTAGTTGCTGTGGGTGCCACAGCTGAAGTCAGTTGTCTTGCTGGTT
    ----+----------+----------+----------+----------+----------+-----
    AGACCTGTCCTTAATCAACGACACCCACGGTGTCGACTTCAGTCAAACAGAACGACCAA
            2970                  2990                  3010
         .         .         .         .         .         .
    TAAATAGATCTTTCAGAGCTGGGTGCTGGGTTTGCCATCTTTTGTTTTCTTTGAAAAGC
    ----+----------+----------+----------+----------+----------+-----
    ATTTATCTAGAAAGTCTCGACCACGACCCAAACGGTAGAAAACAAAAGAAACTTTTCG
            3030                  3050                  3070
         .         .         .         .         .         .
    AGCTTAGTTACCCTTTTTATAAATAAATATCTTGCAGTTAAAAAAAAAAAAAAA
    ----+----------+----------+----------+----------+-------
    TCGAATCAATGGGAAAATATTTATTTTATAGAACGTCAATTTTTTTTTTTTTTT
```

POLYNUCLEOTIDES ENCODING HUMAN DNA LIGASE III AND METHODS OF USING THESE POLYNUCLEOTIDES

This application is a continuation-in-part of International Application PCT/US95/03939, filed 31 Mar. 1995.

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as Human DNA Ligase III. The invention also relates to inhibiting the action of such polypeptides.

DNA strand breaks and gaps are generated transiently during replication, repair and recombination. In mammalian cell nuclei, rejoining of such strand breaks depends on several different DNA polymerases and DNA ligase enzymes.

The mechanism for joining of DNA strand interruptions by DNA ligase enzymes has been widely described. The reaction is initiated by the formation of a covalent enzyme-adenylate complex. Mammalian and viral DNA ligase enzymes employ ATP as cofactor, whereas bacterial DNA ligase enzymes use NAD to generate the adenylyl group. The ATP is cleaved to AMP and pyrophosphate with the adenylyl residue linked by a phosphoramidate bond to the $\epsilon$-amino group of a specific lysine residue at the active site of the protein (Gumport, R. I., et al., *PNAS*, 68:2559–63 (1971)). Reactivated AMP residue of the DNA ligase-adenylate intermediate is transferred to the 5' phosphate terminus of a single strand break in double stranded DNA to generate a covalent DNA-AMP complex with a 5'—5' phosphoanhydride bond. This reaction intermediate has also been isolated for microbial and mammalian DNA ligase enzymes, but is more short lived than the adenylylated enzyme. In the final step of DNA ligation, unadenylylated DNA ligase enzymes required for the generation of a phosphodiester bond catalyze displacement of the AMP residue through attack by the adjacent 3'-hydroxyl group on the adenylylated site.

The occurrence of three different DNA ligase enzymes, DNA Ligase I, II and III, was established previously by biochemical and immunological characterization of purified enzymes (Tomkinson, A. E. et al., *J. Biol. Chem.*, 266:21728–21735 (1991) and Roberts, E., et al., *J. Biol. Chem.*, 269:3789–3792 (1994)). However, the interrelationship between these proteins was unclear as a cDNA clone has only been available for DNA Ligase I, the major enzyme of this type in proliferating cells (Barnes, D. E., et al., PNAS USA, 87:6679–6683 (1990)). The main function of DNA Ligase I appears to be the joining of Okazaki fragments during lagging-strand DNA replication (Waga, S., et al., J. Biol. Chem. 269:10923–10934 (1994); Li, C., et al., Nucl. Acids Res., 22:632–638 (1994); and Prigent, C., et al., Mol. Cell. Biol., 14:310–317 (1994)).

A full-length human cDNA encoding DNA Ligase I has been obtained by functional complementation of a *S. cereviasiae* cdc9 temperature-sensitive DNA ligase mutant (Barker, D. G., *Eur. J. Biochem.*, 162:659–67 (1987)). The full-length cDNA encodes a 102-kDa protein of 919 amino acid residues. There is no marked sequence homology to other known proteins except for microbial DNA ligase enzymes. The active site lysine residue is located at position 568. It also effectively seals single-strand breaks in DNA and joins restriction enzyme DNA fragments with staggered ends. The enzyme is also able to catalyze blunt-end joining of DNA. DNA Ligase I can join oligo (dT) molecules hydrogen-bonded to poly (dA), but the enzyme differs from T4 DNA Ligase II and III in being unable to ligate oligo (dT) with a poly (rA) complementary strand.

Human DNA Ligase III is more firmly associated with the cell nuclei. This enzyme is a labile protein, which is rapidly inactivated at 42° C. DNA Ligase III resembles other eukaryotic DNA Ligase enzymes in requiring ATP as cofactor, but the enzyme differs from DNA Ligase I in having a higher association for ATP. DNA Ligase III catalyzes the formation of phosphodiester bonds with an oligo (dT) ● poly (rA) substrate, but not with an oligo (rA) ● poly (dT) substrate, so it differs completely from DNA Ligase I in this regard (Arrand, J. E. et al., *J. Biol. Chem.*, 261:9079–82 (1986)).

DNA Ligase III repairs single strand breaks in DNA efficiently, but it is unable to perform either blunt-end joining or AMP-dependent relaxation of super-coiled DNA (Elder, R. H. et al., *Eur. J. Biochem.*, 203:53–58 (1992)).

Clues as to the physiological role of DNA Ligase III have come from its physical interaction in a high salt-resistant complex with another nuclear protein, the XRCC1 gene product (Caldecott, K. W., et al., *Mol. Cell. Biol.*, 14:68–76 (1994) and Ljungquist, S., et al., *Mutat. Res.*, 314:177–186 (1994)). The XRCC1 gene encodes a 70 kDa protein, that by itself does not appear to join DNA strand breaks (Caldecott, K. W., et al., *Mol. Cell. Biol.*, 14:68–76 (1994); Ljungquist, S., et al., *Mutat. Res.*, 314:177–186 (1994) and Thompson, L. H., et al., *Mol. Cell. Biol.*, 10:6160–6171 (1990)). However, mutant rodent cells deficient in XRCC1 protein exhibit reduced DNA Ligase III activity, defective strand break repair, an anomalously high level of sister chromatid exchanges, are hyper-sensitive to simple alkylating agents and ionizing radiation, and have an altered mutation spectrum after exposure to ethyl methanesulfonate (Caldecott, K. W., et al., *Mol. Cell. Biol.*, 14:68–76 (1994); Ljungquist, S., et al., *Mutat. Res.*, 314:177–186 (1994); Thompson, L. H., et al., *Mol. Cell. Biol.*, 10:6160–6171 (1990); and Op het Veld, C. W., et al., *Cancer Res.*, 54:3001–3006 (1994)). These data indicate that XRCC1 mutant cells are defective in base excision-repair, and strongly suggest that both DNA Ligase III and XRCC1 are active in this process (Dianov, G., and Lindahl, T., *Curr. Biol.*, 4:1069–1076 (1994)).

A purified mammalian protein fraction active in repair and recombination processes in vitro was shown to contain a ligase with the properties of Human DNA Ligase III, but no detectable amounts of Human DNA Ligase I (Jessberger, R., et al., *J. Biol. Chem.*, 268:15070–15079 (1993)). The role of the distinct enzyme, DNA Ligase II, remains unclear, although an observed increase in DNA Ligase II activity during meiotic prophase suggests a role in meiotic recombination (Higashitani, A., et al., *Cell Struct. Funct.*, 15:67–72 (1990)). Comparison of $^{32}$P-adenylylated DNA Ligase II and III by partial or complete proteolytic cleavage patterns indicated that these two enzymes share extensive amino acid sequence similarity or identity flanking their active sites, but that they are quite different from DNA Ligase I (Roberts, E., et al., *J. Biol. Chem.*, 269:3789–3792 (1994)). Neither DNA Ligase I, II nor III is exclusively a mitochondrial enzyme.

The polynucleotide of the present invention and polypeptide encoded thereby have been putatively identified as human DNA Ligase III as a result of size, amino acid sequence homology to DNA Ligase II and ability to bind XRCC1 protein. Heretofore, the gene sequence of DNA Ligase III was not known.

In accordance with one aspect of the present invention, there are provided novel mature polypeptides which are human DNA Ligase III, as well as biologically active and diagnostically or therapeutically useful fragments, analogs and derivatives thereof.

In accordance with another aspect of the present invention, there are provided isolated nucleic acid molecules encoding human DNA Ligase III, including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptides by recombinant techniques comprising culturing recombinant prokaryotic and/or eukaryotic host cells, containing a human DNA Ligase III nucleic acid sequence, under conditions promoting expression of said protein and subsequent recovery of said protein.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

In accordance with another aspect of the present invention there is provided a method of treating conditions which are related to insufficient human DNA Ligase III activity via gene therapy comprising inserting the DNA Ligase III gene into a patient's cells either in vivo or ex vivo. The gene is expressed in transduced cells and as a result, the protein encoded by the gene may be used therapeutically, for example, to prevent disorders associated with defects in DNA, for example, abnormal cellular proliferation, for example cancers, leukemia and tumors, to treat severe immunosuppression, stunted growth and lymphoma, as well as cellular hypersensitivity to DNA-damaging agents.

In accordance with yet a further aspect of the present invention, there is also provided nucleic acid probes comprising nucleic acid molecules of sufficient length to specifically hybridize to human DNA Ligase III sequences which may be used diagnostically to detect a mutation in the gene encoding DNA Ligase III.

In accordance with yet another aspect of the present invention, there are provided antagonists to such polypeptides, which may be manufactured intracellularly or administered through gene therapy for inhibiting the action of such polypeptides, for example, to target and destroy undesired cells, e.g., cancer cells.

In accordance with still another aspect of the present invention, there are provided diagnostic assays for detecting mutations in the polynucleotide sequences of the present invention for detecting diseases related to a lack of Human DNA Ligase III activity.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1L, collectively, shows the cDNA sequence and the corresponding deduced amino sequence of the DNA Ligase III polypeptide. The standard one letter abbreviation for amino acids is used. The vertical arrow indicates the active site lysine.

In accordance with an aspect of the present invention, there is provided an isolated nucleic acid (polynucleotide, SEQ ID NO:1) which encodes for the mature polypeptide having the deduced amino acid sequence of FIGS. 1A–1L, collectively, shows (SEQ ID No. 2) or for the mature polypeptide encoded by the cDNA of the clone deposited as ATCC Deposit No. 97052 on Feb. 6, 1995.

The ATCC number referred to above is directed to a biological deposit with the ATCC, 12301 Parklawn Drive, Rockville, Md. 20852. The strain is being maintained under the terms of the Budapest Treaty and will be made available to a patent office signatory to the Budapest Treaty.

A polynucleotide encoding a polypeptide of the present invention may be obtained from testis, prostate, heart and thymus. The polynucleotide of this invention was discovered in a cDNA library derived from human testis. It is structurally related to the DNA ligase family. It contains an open reading frame encoding a protein of 922 amino acid residues. The protein exhibits the highest degree of homology to vaccine virus DNA ligase with 56% identity and 73% similarity over the entire protein. It is also important that there is a conserved active lysine residue at position 421 which is bordered on either side by a hydrophobic amino acid residue, and the sequence E-KYDG-R is also conserved and is common to enzymes from different sources such as mammalian cells, yeasts, vaccinia virus and bacteriophage T7.

The region flanking the conserved lysine residue is an active site motif that is essential for the formation of an enzyme-adenylate reaction intermediate (Tomkinson, A. E., et al., *PNAS USA*, 88:400–404 (1991)). The conserved lysine residue is indicated by a vertical arrow and the active site motif is underlined in FIGS. 1A–1L, collectively. Further a putative zinc finger motif shown at residues 18 to 55 in FIGS. 1A–1L, collectively is underlined by a broken line. The 100 kDa in vitro translation product of the DNA ligase III cDNA interacts with human XRCC1 protein which is a characteristic of DNA Ligase III (Caldecott, K. W., et al., *Mol. Cell. Biol.*, 14:68–76 (1994)). Histidine-tagged recombinant XRCC1 protein was incubated with [$^{35}$S] methionine-labelled in vitro translation product of the cDNA to allow formation of XRCC1-protein complexes, after which NTA-agarose beads were added to affinity-bind XRCC1-His. The agarose beads were washed to remove non-specifically associated polypeptides prior to elution of XRCC1-His with 200 mM imidazole. XRCC1-his binds the product of the cDNA. Recovery of radiolabeled polypeptides is dependent on addition of XRCC1-His. Approximately 50% of the full length 100 kDa translation product, and as much as 90% of some of the truncated polypeptides, were recovered with XRCC1-His. These results indicate that the cDNA clone encodes a 100 kDa polypeptide.

The longest open reading frame of the cDNA encoding DNA ligase III extends from 73 bp to 3099 bp within the cDNA clone and would encode a polypeptide of 1009 amino acids, approximately 150 kDa molecular mass. The next downstream ATG at 334 bp occurs in a typical translation start consensus and defines an open reading frame of 2766 bp (922 amino acids). The protein produced in this case would be approximately 103 kDa, consistent with both the observed molecular mass of the in vitro translation product and the apparent molecular mass of authentic DNA Ligase III purified from HeLa cells by standard chromatographic procedures. This indicates that this cDNA represents a full length cDNA clone. Furthermore, a 5'-truncated cDNA clone lacking the first 78 bp (and the first ATG codon) produced an in vitro translation product of identical electrophoretic mobility to that encoded by the full length clone, in support of assignment of the ATG at 334 bp as the translation initiation codon.

The DNA Ligase III amino acid sequence shows extensive amino acid homology to Human DNA Ligase I. The DNA Ligase III sequence is identical at 8 of 12 residues flanking the active site lysine of DNA Ligase I, and both contain the minimum active site consensus for all ATP-dependent DNA ligases, -K-DG-R-, with $lys_{421}$ (DNA Ligase III) being the putative active lysine. Although their amino acid sequences are not colinear at optimum alignment, human DNA Ligase I and III differ by 9 amino acids in the size of the region between the two motifs (active lysine and minimum active site motifs).

The 3' flanking motif is located 37 amino acids from the C-terminus of DNA Ligase I, whereas the DNA Ligase III sequence extends a further 195 residues. The C-terminus of the DNA Ligase III shows weak homology to several proteins, including approximately 20% identity to a 144 amino acid sequence within the C-terminal quarter of both human and murine XRCC1.

In their N-terminal regions, DNA Ligase I and III show very limited sequence homology beyond about 30 residues upstream of their active sites, and DNA Ligase I has an extended hydrophilic N-terminal region with no homology to DNA Ligase.

The N-terminal 112 amino acids of the DNA Ligase III cDNA show approximately 30% identity to residues 3 to 107, and also residues 108 to 217, of human poly (ADP ribose) polymerase (PARP). These same two regions contain two evolutionarily conserved zinc finger motifs within the DNA-binding domain of PARP.

The highly conserved motif flanking the 3' boundary of the region of homology between DNA Ligase I and III is unique to ATP-dependent DNA ligases and is not found in the RNA capping enzymes. Similarly to vaccinia virus DNA Ligase, Human DNA Ligase III does not contain the region 2 motif which is present in the capping enzymes, and Human DNA Ligase I (Shuman, S., et al. PNAS USA, in press (1994)).

There is near identity of peptides within the predicted amino acid sequence of the DNA Ligase III cDNA with sequenced tryptic peptides from the 70 kDa bovine DNA Ligase II protein (Wang, Y-C. J., et al., *J. Biol. Chem.*, 269:31923–31928 (1994)). These tryptic peptides span the region between the active site and the conserved DNA Ligase-specific motif, and are also highly homologous to the corresponding region of the vaccinia virus DNA ligase. The sequence $_{411}$-(K) CPNGMFSEIKYDGERVQVH (K)-$_{431}$ (SEQ ID No. 9) in the DNA ligase III cDNA, with $Lys_{421}$ the putative active lysine, is identical to the active site tryptic peptide identified in the purified bovine DNA Ligase II protein and different from that of DNA Ligase I (Tomkinson, A. E., et al., *PNAS USA*, 88:400–404 (1991)).

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1L, collectively, (SEQ ID No. 1) or that of the deposited clone or may be a different coding sequence which coding sequence, as a result of the redundancy or degeneracy of the genetic code, encodes the same mature polypeptide as the DNA of FIGS. 1A–1L, collectively, (SEQ ID No. 1) or the deposited cDNA.

The polynucleotide which encodes for the mature polypeptide of FIGS. 1A–1L, collectively, (SEQ ID No. 2) or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1L, collectively, (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1L, collectively, (SEQ ID No. 2) or the same mature polypeptide encoded by the cDNA of the deposited clone as well as variants of such polynucleotides which variants encode for a fragment, derivative or analog of the polypeptide of FIGS. 1A–1L, collectively, (SEQ ID No. 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1L, collectively, (SEQ ID No. 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., *Cell,* 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1L, collectively, (SEQ ID NO:1) or the deposited cDNA (s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a DNA Ligase III polypeptide which has the deduced amino acid sequence of FIGS. 1A–1L, collectively, (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIGS. 1A–1L, collectively, (SEQ ID No. 2) or that encoded by the deposited cDNA, means a polypeptide which retains essentially the same biological function or activity as such polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1L, collectively, (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, which is employed for purification of the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "gene" means the segment of DNA involved in producing a polypeptide chain; it includes regions preceding and following the coding region (leader and trailer) as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the DNA Ligase III genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, PNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation, initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The DNA Ligase III polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The DNA Ligase III polypeptides and agonists and antagonists which are polypeptides, described below, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Once the DNA Ligase III polypeptide is being expressed intracellularly via gene therapy, it may be used to repair single-strand breaks in DNA which result from DNA-damaging agents, e.g., UV radiation. Several human syndromes result from autosomal recessive inheritance for the DNA ligase gene. These syndromes cause severe immunodeficiency and greatly increases the susceptibility of abnormal cellular differentiation due to the disrepair of DNA while at the cellular level they are characterized by chromosome instability and hypersensitivity to DNA-damaging agents. These syndromes include Fanconi's anemia and Blackfan-diamond anemia.

The polypeptide of the present invention may also be employed to treat severe immunosuppression which is the result of a defect in the DNA Ligase III gene. DNA Ligase III may also be employed to treat stunted growth and lymphoma which result from defective rejoining of DNA.

Chromosome abnormalities in the 17q11-12 region, to which the DNA Ligase III gene has been mapped, are associated with several diseases including several neoplasias. The most common neoplastic chromosomal abnormality in this region is a translocation between chromosomes 15 and 17 seen in acute myeloid leukemia subtype m3 which involves the disruption of the retinoic acid receptor α gene (Chomienne, H., et al., *Nature,* 347:558–561 (1990)). However, chromosomal abnormalities in this region are frequently reported in both acute myeloid and lymphoblastic leukemias and are seen sporadically in several other cancers (Mitelman, F., Catalog of Chromosome Aberrations in Cancer (Fourth Edition), Wiley Liss, New York (1991)). Accordingly, the DNA Ligase III gene and gene product may be employed to treat these neoplasias.

Fragments of the full length Ligase III gene may be used as a hybridization probe for a cDNA library to isolate other genes which have a high sequence similarity to the DNA Ligase III gene or have similar biological activity. Probes of this type have at least 20 bases. Preferably, however, the probes have at least 30 bases and may contain, for example, 50 or more bases. The probe may also be used to identify a cDNA clone corresponding to a full length transcript and a genomic clone or clones that contain the complete DNA Ligase III gene including regulatory and promotor regions, exons, and introns.

An example of a screen comprises isolating the coding region of the DNA Ligase III gene by using the known DNA sequence to synthesize an oligonucleotide probe. Labelled oligonucleotides having a sequence complementary to that of the gene of the present invention are used to screen a library of human cDNA, genomic DNA or mRNA to determine which members of the library the probe hybridizes to.

The polypeptide and/or polynucleotide of the present invention may also be employed in relation to scientific research, synthesis of DNA and for the manufacture of DNA vectors. The polypeptide and/or polynucleotide of the present invention may be sold into the research market. Thus, for example DNA Ligase III may be used for ligation of DNA sequences in vitro in a manner similar to other DNA ligase enzymes of the art.

This invention also provides a method of screening compounds to identify those which enhance or inhibit the DNA-joining reaction catalyzed by human DNA Ligase III. An example of such a method comprises combining ATP, DNA Ligase III and DNA having single-strand breaks with the compound under conditions where the DNA Ligase would normally cleave ATP to AMP and the AMP is transferred to the 5' phosphate terminus of a single strand break in double-stranded DNA to generate a covalent DNA-AMP complex with the single strand break being subsequently repaired. The DNA having the single-strand breaks may be supplied in the above example by mutant cells which are deficient in proteins that are responsible for strand break repair, for example, mutant rodent cells deficient in XRCC1 and the cdc9 *S. Cerevisiae* DNA ligase mutant. The ability of the compound to enhance or block the catalysis of this reaction could then be measured to determine if the compound is an effective agonist or antagonist.

Human DNA Ligase III is produced and functions intracellularly, therefore, any antagonist must be intracellular. Potential antagonists to human DNA Ligase III include antibodies which are produced intracellularly. For example, an antibody identified as antagonizing DNA Ligase III may be produced intracellularly as a single chain antibody by procedures known in the art, such as transforming the appropriate cells with DNA encoding the single chain antibody to prevent the function of human DNA Ligase III.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of DNA Ligase III. The antisense RNA oligonucleotide hybridizes to the mRNA in vivo and blocks translation of the mRNA molecule into the DNA Ligase III (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of DNA Ligase III.

Yet another potential antagonist includes a mutated form, or mutein, of DNA Ligase III which recognizes DNA but does not repair single-strand breaks and, therefore, acts to prevent human DNA Ligase III from functioning.

The antagonists may be employed to target undesired cells, e.g., cancer cells and leukemic cells, since the prevention of DNA Ligase III prevents repair of single-strand breaks in DNA and will eventually result in death of the cell.

The small molecule agonists and antagonists of the present invention may be employed in combination with a suitable pharmaceutical carrier. Such compositions comprise a therapeutically effective amount of the molecule and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

This invention also provides the use of the human DNA Ligase III gene as a diagnostic. For example, some diseases result from inherited defective genes. These genes can be detected by comparing the sequence of the defective gene with that of a normal one. That is, a mutant gene would be associated with hypersensitivity to DNA-damaging agents and an elevated susceptibility to abnormal cell growth, for example, tumors, leukemia and cancer.

Individuals carrying mutations in the human DNA Ligase III gene may be detected at the DNA level by a variety of techniques. Nucleic acids used for diagnosis may be obtained from a patient's cells, such as from blood, urine, saliva, tissue biopsy and autopsy material. The genomic DNA may be used directly for detection or may be amplified enzymatically by using PCR (Saiki et al., *Nature*, 324:163–166 (1986)) prior to analysis. RNA or cDNA may also be used for the same purpose. Deletions or insertions can be detected by a change in size of the amplified product in comparison to the normal genotype. Point mutations can be identified by hybridizing amplified DNA to radiolabeled DNA Ligase III RNA or alternatively, radiolabeled DNA Ligase III antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase protection and S1 protection or the chemical cleavage method (e.g., Cotton et al., *PNAS, USA*, 85:4397–4401 (1985)).

Thus, the detection of a specific DNA sequence may be achieved by methods such as hybridization, RNase protection, chemical cleavage, direct DNA sequencing, or the use of restriction enzymes, e.g., restriction fragment length polymorphisms, and Southern blotting of genomic DNA. Also, mutations may be detected by in situ analysis.

In addition, some diseases are a result of, or are characterized by, changes in gene expression which can be detected by changes in the mRNA. Alternatively, the DNA Ligase III gene can be used as a reference to identify individuals expressing a decreased level of DNA Ligase III protein, e.g., by Northern blotting.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Detailed analysis of 19 individual chromosomes using a combination of fractional length measurements and fluorescent binding combined with high-resolution image analysis indicated that Human DNA Ligase III is located within bands 17q11.2-12.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The gene of the present invention has been mapped to chromosome 13q33-34.

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of DNA Ligase III

The DNA sequence encoding DNA Ligase III, ATCC # 97052, is initially amplified using PCR oligonucleotide primers corresponding to the 5' and 3' end sequences of the processed DNA Ligase III gene. The 5' oligonucleotide primer has the sequence 5' CGC GGATCCATGGCTGAGCAACGGTTCTG 3' (SEQ ID No. 3) contains a Bam HI restriction enzyme site (underlined)

followed by 20 nucleotides of DNA Ligase III coding sequence starting from the presumed terminal amino acid of the processed protein codon. The 3' sequence 5' GCG TCTAGACTAGCAGGGAGCTACCAG 3' (SEQ ID No. 4) contains complementary sequences to a XbaI site (underlined) and is followed by 18 nucleotides of DNA Ligase III at C-terminal of DNA Ligase III. The restriction enzyme sites correspond to the restriction enzyme sites on the bacterial expression vector pQE-9 (Qiagen, Inc. Chatsworth, Calif.). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 is then digested with Bam HI and Pst I. The amplified sequences are ligated into pQE-9 and inserted in frame with the sequence encoding for the histidine tag and the RBS. The ligation mixture is then used to transform *E. coli* strain M15/rep 4 (Qiagen, Inc.) under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized protein extract is purified from this solution by chromatography on a Nickel-Chelate column under conditions that allow for tight binding by proteins containing the 6-His tag (Hochuli, E. et al., J. Chromatography 411:177–184 (1984)) and eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2

Cloning and Expression of DNA Ligase III Using the Baculovirus Expression System A DNA sequence encoding full length DNA Ligase III protein, ATCC # 97052, is amplified using PCR oligonucleotide primers corresponding to the 5' and 3' sequences of the gene:

The 5' primer has the sequence 5' CGCGAATCC ATGGCTGAGCAACGGTTCTG 3' (SEQ ID No. 5) and contains a BamHI restriction enzyme site (in bold) followed first by 20 nucleotides of N-terminal sequence (the initiation codon for translation "ATG" is underlined).

The 3' primer has the sequence 5' GCG TCTAGACTAGCAGGGAGCTACCAG 3' (SEQ ID No. 6) and contains the cleavage site for the restriction endonuclease XbaI (in bold) and 18 nucleotides complementary to the C-terminal sequence of the DNA Ligase III gene. The amplified sequences were isolated from a 1% agarose gel using a commercially available kit ("Geneclean," BIO 101 Inc., La Jolla, Calif.). The fragment was then digested with the endonucleases BamHI and XbaI and then purified again on a 1% agarose gel. This fragment is designated F2.

The vector pA2 (modification of pVL941 vector, discussed below) is used for the expression of the DNA Ligase III protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhidrosis virus (AcMNPV) followed by the recognition sites for the restriction endonucleases BamHI and XbaI. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. *E. coli* HB101 cells are then transformed and bacteria identified that contained the plasmid (pBac DNA Ligase III) with the DNA Ligase III gene using the enzymes BamHI and XbaI. The sequence of the cloned fragment is confirmed by DNA sequencing.

5 $\mu$g of the plasmid pBac DNA Ligase III was cotransfected with 1.0 $\mu$g of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 $\mu$g of BaculoGold™ virus DNA and 5 $\mu$g of the plasmid pBac DNA Ligase III are mixed in a sterile well of a microtiter plate containing 50 $\mu$l of serum free Grace's medium (Life Technologies Inc., Gaithersburg, Md.). Afterwards 10 $\mu$l Lipofectin plus 90 $\mu$l Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-DNA Ligase III at a multiplicity of infection (MOI) of 2. Six hours later the medium is removed and replaced with SF900 III medium minus methionine and cysteine (Life Technologies Inc., Gaithersburg). 42 hours later 5 µCi of $^{35}$S-methionine and 5 µCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant DNA Ligase III in COS Cells

The expression of plasmid, DNA Ligase III HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire DNA Ligase III precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, Cell 37:767 (1984)). The infusion of HA tag to the target protein allows detection of the recombinant protein with an antibody that recognizes the HA epitope.

The plasmid construction strategy is described as follows:

The DNA sequence encoding DNA Ligase III, ATCC # 97052, is constructed by PCR using two primers: the 5' primer 5' CGC<u>GAATCC</u>ATGGCTGAGCAACGGTTCTG 3' (SEQ ID No. 7) contains an BamHI site (underlined) followed by 20 nucleotides of DNA Ligase III coding sequence starting from the initiation codon; the 3' sequence 5' GCG<u>TCTAGA</u>TCAAGCGTAGTCTGGGACGTC GTATGGGTAGCAGGGAGCTACCAGTC 3' (SEQ ID No. 8) contains complementary sequences to an XbaI site (underlined), translation stop codon, HA tag and the last 17 nucleotides of the DNA Ligase III coding sequence (not including the stop codon). Therefore, the PCR product contains an BamHI site, DNA Ligase III coding sequence followed by HA tag fused in frame, a translation termination stop codon next to the HA tag, and an XbaI site. The PCR amplified DNA fragment and the vector, pcDNAI/Amp, are digested with BamHI and XbaI restriction enzyme and ligated. The ligation mixture is transformed into E. coli strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant DNA Ligase III, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the DNA Ligase III HA protein is detected by radiolabeling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 4

Expression Pattern of DNA Ligase III in Human Tissue

Northern blot analysis may be performed to examine the levels of expression of DNA Ligase III in human tissues. Total cellular RNA samples are isolated with RNAzol™ B system (Biotecx Laboratories, Inc. Houston, Texas) About 15 µg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with song DNA fragment. The labeled DNA is purified with a Select-G-50 column (5 Prime-3 Prime, Inc. Boulder, Colo.). The filter containing the particular RNA blot is then hybridized with radioactive labeled full length DNA Ligase III gene at 1,000,000 cpm/ml in 0.5M NaPO$_4$, pH 7.4 and 7% SDS overnight at 65° C. After wash twice at room temperature and twice at 60° C. with 0.5×SSC, 0.1% SDS, the filter is then exposed at −70° C. overnight with an intensifying screen. The message RNA for DNA Ligase III is abundant in the testis, prostate, heart, thymus.

EXAMPLE 5

In vitro Transcription/Translation of cDNA Clones

Putative full-length cDNA clone was subcloned as follows: DNA ligase III was subcloned as a Sal I/Not I restriction fragment into the multiple cloning sire of pSPORT (Life Technologies), with the 5' end proximal to the T7 promoter; the DNA ligase III plasmid constructs (1 µg) was linearized with either Not I or Xho I (New England Biolabs), downstream of the cDNA insert, then transcribed and capped at 36° C. for 30 minutes with T7 polymerase and the mCAP RNA capping kit (Stratagene). The reactions were terminated by incubation with 10 units RNase-free DNase at 37° C. for 5 minutes. Following phenol/chloroform extraction and ethanol precipitation, the in vitro transcription products were resuspended in 20 µl 10 mM Tris-HCl/1 nM EDTA, pH 8.0 (TE). The transcript (0 to 5 µl, made up to a final volume of 5 µl with water) was translated in 20 µl rabbit reticulocyte lysate (Amersham) at 30° C. for 90 minutes. In order to radiolabel the product of in vitro translation, reaction was supplemented with 20 µCi [$^{35}$S] methionine (3000 Ci mmol$^{-1}$, Amersham). Translations were terminated by incubation with 5 µl of 400 ml$^{-1}$ RNase A/50 mM EDTA at 37° C. for 15 minutes (30 µl final volume). Samples (5 µl) of translations carried out in the presence of [$^{35}$S]methionine were analyzed by electrophoresis in SDS-7.5% polyacrylamide gels and autoradiography. Non-radiolabeled translation products were assayed for ability to form protein-adenylate complexes after removal of ATP by chromatography through spun 1 ml columns of Sephadex G50 (Pharmacia) equilibrated with TE.

EXAMPLE 6

DNA Ligase Assays

5 µl samples from in vitro translations were adenylylated in reaction mixtures (30 µl) containing 60 mM Tris HCl (pH 8.0), 10 mM $MgCl_2$, 50 µg $ml^{-1}$ BSA, 5 mM DTT and 1 µCi $[\alpha^{-32}P]$ ATP (3000 Ci $mmol^{-1}$ Amersham) at 20° C. for 10 minutes and then analyzed by electrophoresis in SDS-7.5% polyacrylamide gels and autoradiography. In order to monitor transfer of $[^{32}p]$AMP from protein-adenylate to a nicked DNA substrate, 5 µl samples from adenylylation reactions were incubated for further time periods with or without the addition of 500 ng non-radiolabeled oligo$(dT)_{16}$-poly(dA), as described previously. The ability to transfer $[^{32}P]$AMP from enzyme-adenylate to the hybrid substrates, oligo(dT)-poly(rA) or oligo(rA)-poly(dT), differentiates DNA ligase I, II and III. However, both these latter substrates were rapidly degraded by an RNase H activity upon incubation in the reticulocyte lysate, even when mixtures were used directly without termination of translation reactions by addition of RNase A.

EXAMPLE 7

Expression of DNA Ligase III Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

Moloney murine leukemia virus is digested and treated with calf intestinal phosphatase. The linear vector is fractionated on agarose gel and purified, using glass beads.

The DNA Ligase III cDNA (see FIG. 1), is isolated and the ends of this fragment are treated with DNA polymerase in order to fill in the recessed ends and create blunt ends.

Equal quantities of the Moloney murine leukemia virus linear backbone and the gene are added together, in the presence of T4 DNA ligase. The resulting mixture is maintained under conditions appropriate for ligation of the two fragments. The ligation mixture was used to transform bacteria HB101, which were then plated onto agar-containing kanamycin for the purpose of confirming that the vector had the DNA Ligase III gene properly inserted.

PE501 packaging cells are grown in tissue culture to confluent density in Dulbecco's Modified Eagles Medium (DMEM) with 10% calf serum (CS), penicillin and streptomycin. The Moloney murine leukemia virus vector containing the gene is then added to the media and the packaging cells are transduced with the vector. The packaging cells now produce infectious viral particles containing the DNA Ligase III gene.

Fresh media is added to the transduced producer cells, and subsequently the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells.

The engineered fibroblasts are then injected into the into a host, for example, a rat, either alone or after having been grown to confluence on cytodex 3 microcarrier beads. The fibroblasts now produce the protein product and the biological actions of DNA Ligase III are conveyed to the host.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least 95% identity to a member selected from the group consisting of:
    (a) a polynucleotide encoding a polypeptide comprising the amino acid sequence from amino acid 2 to 922 of SEQ ID NO:2; and
    (b) the complement of (a).

2. The isolated polynucleotide of claim 1 wherein said member is (a).

3. The isolated polynucleotide of claim 1 wherein said member is (a) and the polypeptide comprises amino acids 1 to 922 of SEQ ID No:2.

4. The isolated polynucleotide of claim 1 comprising a polynucleotide encoding a polypeptide comprising the amino acid sequence identical to amino acids 2 to 922 of SEQ ID NO:2.

5. The isolated polynucleotide of claim 1 comprising a polynucleotide encoding a polypeptide comprising the amino sequence identical to amino acids 1 to 922 of SEQ ID NO:2.

6. The isolated polynucleotide of claim 1, wherein said polynucleotide is RNA.

7. The isolated polynucleotide of claim 2, wherein the polynucleotide is DNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2, wherein said polynucleotide is DNA.

11. A method for producing a polypeptide comprising expressing from the recombinant cell of claim 10 the polypeptide encoded by said polynucleotide, wherein said polypeptide has DNA ligase III activity.

12. A process for producing a polypeptide comprising:
    expressing from a recombinant cell containing the polynucleotide of claim 4 the polypeptide encoded by said polynucleotide.

13. The isolated polynucleotide of claim 4 comprising nucleotides 337 to 3099 of SEQ ID NO:1.

14. The isolated polynucleotide of claim 4 comprising nucleotides 334 to 3099 of SEQ ID NO:1.

15. A process for producing a polypeptide comprising:
    expressing from a recombinant cell containing the polynucleotide of claim 5 the polypeptide encoded by said polynucleotide.

16. An isolated polynucleotide comprising a polynucleotide having at least a 95% identity to a member selected from the group consisting of:
    (a) a polynucleotide encoding the same mature polypeptide encoded by the human cDNA in ATCC Deposit No. 97052; and
    (b) the complement of (a).

17. The isolated polynucleotide of claim 16, wherein the member is (a).

18. A process for producing a polypeptide comprising expressing from a recombinant host cell the polypeptide encoded by the polynucleotide according to claim 17, wherein said polypeptide has DNA ligase III activity.

19. The isolated polynucleotide of claim 16, wherein said polynucleotide comprises DNA identical to the coding portion of the human cDNA in ATCC Deposit No. 97052 which encodes a mature polypeptide.

\* \* \* \* \*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3417 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
CCACGCGTCC    GGCAGCCTGT    ATGAGCAAGT    GCCGAGGCCT    ACGGTGAGCG    CCGGAGCCGG        6 0

AGAGGCAGCT    ATATGTCTTT    GGCTTTCAAG    ATCTTCTTTC    CACAAACCCT    CCGTGCACTC        1 2 0
```

| | | | | | |
|---|---|---|---|---|---|
| AGCCGAAAAG | AACTGTGCCT | ATTCCGAAAA | CATCACTGGC | GTGATGTAAG | ACAATTCAGC | 180 |
| CAGTGGTCAG | AAACAGATCT | GCTTCATGGA | CATCCCTCT | TCCTGAGAAG | AAAGCCTGTT | 240 |
| CTATCATTCC | AGGGAAGCCA | TCTAAGATCA | CGTGCCACCT | ACCTTGTTTT | CTTGCCAGGG | 300 |
| TTGCATGTGG | GACTCTGCAG | TGGCCCCTGT | GAGATGGCTG | AGCAACGGTT | CTGTGTGGAC | 360 |
| TATGCCAAGC | GTGGCACAGC | TGGCTGCAAA | AAATGCAAGG | AAAGATTGT | GAAGGGCGTA | 420 |
| TGCCGAATTG | GCAAAGTGGT | GCCCAATCCC | TTCTCAGAGT | CTGGGGGTGA | TATGAAAGAG | 480 |
| TGGTACCACA | TTAAATGCAT | GTTTGAGAAA | CTAGAGCGGG | CCCGGGCCAC | CACAAAAAAA | 540 |
| ATCGAGGACC | TCACAGAGCT | GGAAGGCTGG | GAAGAGCTGG | AAGATAATGA | GAAGGAACAG | 600 |
| ATAACCCAGC | ACATTGCAGA | TCTGTCTTCT | AAGGCAGCAG | GTACACCAAA | GAAGAAAGCT | 660 |
| GTTGTCCAGG | CTAAGTTGAC | AACCACTGGC | CAGGTGACTT | CTCCAGTGAA | AGGCGCCTCA | 720 |
| TTTGTCACCA | GTACCAATCC | CCGGAAATTT | TCTGGCTTTT | CAGCCAAGCC | CAACAACTCT | 780 |
| GGGGAAGCCC | CCTCGAGCCC | CACCCCTAAG | AGAAGTCTGT | CTTCAAGCAA | ATGTGACCCC | 840 |
| AGGCATAAGG | ACTGTCTGCT | ACGGGAGTTT | CGAAAGTTAT | GCGCCATGGT | GGCCGATAAT | 900 |
| CCTAGCTACA | ACACGAAGAC | CCAGATCAGC | CAGGACTTCC | TTCGGAAAGG | CTCAGCAGGA | 960 |
| GATGGTTTCC | ACGGTGATGT | GTACCTAACA | GTGAAGCTGC | TGCTGCCAGG | AGTCATTAAG | 1020 |
| ACTGTTTACA | ACTTGAACGA | TAAGCAGATT | GTGAAGCTTT | TCAGTCGCAT | TTTTAACTGC | 1080 |
| AACCCAGATG | ATATGGCACG | GGACCTAGAG | CAGGGTGACG | TGTCAGAGAC | AATCAGAGTC | 1140 |
| TTCTTTGAGC | AGAGCAAGTC | TTTCCCCCCA | GCTGCCAAGA | GCCTCCTTAC | CATCCAGGAA | 1200 |
| GTGGATGAGT | TCCTTCTGCG | GCTGTCCAAG | CTCACCAAGG | AGGATGAGCA | GCAACAGGCC | 1260 |
| CTACAGGACA | TTGCCTCCAG | GTGTACAGCC | AATGACCTTA | AATGCATCAT | CAGGTTGATC | 1320 |
| AAACATGATC | TGAAGATGAA | CTCAGGTGCA | AAACATGTGT | TAGACGCCCT | TGACCCCAAT | 1380 |
| GCCTATGAAG | CCTTCAAAGC | CTCGCGCAAC | CTGCAGGATG | TGGTGGAGCG | GGTCCTTCAC | 1440 |
| AACGCGCAGG | AGGTGGAGAA | GGAGCCGGGC | CAGAGACGAG | CTCTGAGCGT | CCAGGCCTCG | 1500 |
| CTGATGACAC | CTGTGCAGCC | CATGTTGGCG | GAGGCCTGCA | AGTCCGTTGA | GTATGCAATG | 1560 |
| AAGAAATGTC | CCAATGGCAT | GTTCTCTGAG | ATCAAGTACG | ATGGAGAGCG | AGTCCAGGTG | 1620 |
| CATAAGAATG | GAGACCACTT | CAGCTACTTC | AGCCGCAGTC | TCAAGCCCGT | CCTTCCTCAC | 1680 |
| AAGGTGGCCC | ACTTTAAGGA | CTACATTCCC | CAGGCTTTTC | CTGGGGGCCA | CAGCATGATC | 1740 |
| TTGGATTCTG | AAGTGCTTCT | GATTGACAAC | AAGACAGGCA | AACCACTGCC | CTTTGGGACT | 1800 |
| CTGGGAGTCA | CACCGAAAGC | AGCCTTCCAG | GATGCTAATG | TCTGCCTGTT | TGTTTTTGAT | 1860 |
| TGTATCTACT | TTAATGATGT | CAGCTTGATG | GACAGACCTC | TGTGTGAGCG | GCGGAAGTTT | 1920 |
| CTTCATGACA | ACATGGTTGA | AATTCCAAAC | CGGATCATGT | TCTCAGAAAT | GAAGCGAGTC | 1980 |
| ACAAAGCTT | TGGACTTGGC | TGACATGATA | ACCCGGGTGA | TCCAGGAGGG | ATTGGAGGGG | 2040 |
| CTGGTGCTGA | AGGATGTGAA | GGGTACATAT | GAGCCTGGGA | AGCGGCACTG | GCTGAAAGTG | 2100 |
| AAGAAAGACT | ATTTGAACGA | GGGGGCCATG | GCCGACACAG | CTGACCTGGT | GGTCCTTGGA | 2160 |
| GCCTTCTATG | GGCAAGGGAG | CAAAGGCGGC | ATGATGTCAA | TCTTCCTCAT | GGGCTGCTAC | 2220 |
| GACCCTGGCA | GCCAGAAGTG | GTGCACAGTC | ACCAAGTGTG | CAGGAGGCCA | TGATGATGCC | 2280 |
| ACGCTTGCCC | GCCTGCAGAA | TGAACTAGAC | ATGGTGAAGA | TCAGCAAGGA | CCCCAGCAAA | 2340 |
| ATACCCAGCT | GGTTGAAGGT | CAACAAGATC | TACTATCCTG | ACTTCATCGT | CCCAGACCCA | 2400 |
| AAGAAAGCTG | CCGTGTGGGA | GATCACAGGG | GCTGAATTCT | CCAAATCGGA | GGCTCATACA | 2460 |
| GCTGACGGGA | TCTCCATCCG | ATTCCCTCGC | TGCACCCGAA | TCCGAGATGA | TAAGGACTGG | 2520 |

|                                                                                              |      |
| -------------------------------------------------------------------------------------------- | ---- |
| AAATCTGCCA  CTAACCTTCC  CCAACTCAAG  GAACTGTACC  AGTTGTCCAA  GGAGAAGGCA                        | 2580 |
| GACTTCACTG  TAGTGGCTGG  AGATGAGGGG  AGCTCCACTA  CAGGGGGTAG  CAGTGAAGAG                        | 2640 |
| AATAAGGGTC  CCTCAGGGTC  TGCTGTGTCC  CGCAAGGCCC  CCAGCAAGCC  CTCAGCCAGT                        | 2700 |
| ACCAAGAAAG  CAGAAGGGAA  GCTGAGTAAC  TCCAACAGCA  AAGATGGCAA  CATGCAGACT                        | 2760 |
| GCAAAGCCTT  CCGCTATGAA  GGTGGGGGAG  AAGCTGGCCA  CAAAGTCTTC  TCCAGTGAAA                        | 2820 |
| GTAGGGGAGA  AGCGGAAAGC  TGCTGATGAG  ACGCTGTGCC  AAACAAGGT  ATTGCTGGAC                         | 2880 |
| ATCTTCACTG  GGGTGCGGCT  TTACTTGCCA  CCCTCCACAC  CAGACTTCAG  CCGTCTCAGA                        | 2940 |
| CGCTACTTTG  TGGCATTCGA  CGGGGACCTG  GTACAGGAAT  TTGATATGAC  TTCAGCCACG                        | 3000 |
| CACGTGCTGG  GTAGCAGGGA  CAAGAACCCT  GCGGCCCAGC  AGGTCTCCCC  AGAGTGGATT                        | 3060 |
| TGGGCATGTA  TCCGGAAACG  GAGACTGGTA  GCTCCCTGCT  AGGTTTGCTG  TCTTCCCTCT                        | 3120 |
| CCCTCAGGCC  ATACTCTCCT  TTACCATACT  ATTGGACTGG  ACTCAGGCTG  GAGGCAGATA                        | 3180 |
| GACACAGTAT  AGGGGGAATG  GGCTTGCTTC  TCCCAAACCC  ACCAGTTCTC  CACTGTCTCT                        | 3240 |
| TCTGGACCAG  GAATTAGTTG  CTGTGGGTGC  CACAGCTGAA  GTCAGTTTGT  CTTGCTGGTT                        | 3300 |
| TAAATAGATC  TTTCAGAGCT  GGGTGCTGGG  TTTGCCATCT  TTTTGTTTTC  TTTGAAAAGC                        | 3360 |
| AGCTTAGTTA  CCCTTTTTAT  AAATAAAATA  TCTTGCAGTT  AAAAAAAAAA  AAAAAA                            | 3417 |

( 2 ) INFORMATION FOR SEQ ID NO:2:

( i ) SEQUENCE CHARACTERISTICS:
        ( A ) LENGTH: 922 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met  Ala  Glu  Gln  Arg  Phe  Cys  Val  Asp  Tyr  Ala  Lys  Arg  Gly  Thr
                    5                        10                       15

Ala  Gly  Cys  Lys  Lys  Cys  Lys  Glu  Lys  Ile  Val  Lys  Gly  Val  Cys
                    20                       25                       30

Arg  Ile  Gly  Lys  Val  Val  Pro  Asn  Pro  Phe  Ser  Glu  Ser  Gly  Gly
                    35                       40                       45

Asp  Met  Lys  Glu  Trp  Tyr  His  Ile  Lys  Cys  Met  Phe  Glu  Lys  Leu
                    50                       55                       60

Glu  Arg  Ala  Arg  Ala  Thr  Thr  Lys  Lys  Ile  Glu  Asp  Leu  Thr  Glu
                    65                       70                       75

Leu  Glu  Gly  Trp  Glu  Glu  Leu  Glu  Asp  Asn  Glu  Lys  Glu  Gln  Ile
                    80                       85                       90

Thr  Gln  His  Ile  Ala  Asp  Leu  Ser  Ser  Lys  Ala  Ala  Gly  Thr  Pro
                    95                       100                      105

Lys  Lys  Lys  Ala  Val  Val  Gln  Ala  Lys  Leu  Thr  Thr  Thr  Gly  Gln
                    110                      115                      120

Val  Thr  Ser  Pro  Val  Lys  Gly  Ala  Ser  Phe  Val  Thr  Ser  Thr  Asn
                    124                      130                      135

Pro  Arg  Lys  Phe  Ser  Gly  Phe  Ser  Ala  Lys  Pro  Asn  Asn  Ser  Gly
                    140                      145                      150

Glu  Ala  Pro  Ser  Ser  Pro  Thr  Pro  Lys  Arg  Ser  Leu  Ser  Ser  Ser
                    155                      160                      165

Lys  Cys  Asp  Pro  Arg  His  Lys  Asp  Cys  Leu  Leu  Arg  Glu  Phe  Arg
                    170                      175                      180

Lys  Leu  Cys  Ala  Met  Val  Ala  Asp  Asn  Pro  Ser  Tyr  Asn  Thr  Lys
```

```
                                    185                             190                             195
Thr  Gln  Ile  Ile  Gln  Asp  Phe  Leu  Arg  Lys  Gly  Ser  Ala  Gly  Asp
                         200                            205                             210
Gly  Phe  His  Gly  Asp  Val  Tyr  Leu  Thr  Val  Lys  Leu  Leu  Leu  Pro
                         215                            220                             225
Gly  Val  Ile  Lys  Thr  Val  Tyr  Asn  Leu  Asn  Asp  Lys  Gln  Ile  Val
                         230                            235                             240
Lys  Leu  Phe  Ser  Arg  Ile  Phe  Asn  Cys  Asn  Pro  Asp  Asp  Met  Ala
                         245                            250                             255
Arg  Asp  Leu  Glu  Gln  Gly  Asp  Val  Ser  Glu  Thr  Ile  Arg  Val  Phe
                         260                            265                             270
Phe  Glu  Gln  Ser  Lys  Ser  Phe  Pro  Pro  Ala  Ala  Lys  Ser  Leu  Leu
                         275                            280                             285
Thr  Ile  Gln  Glu  Val  Asp  Glu  Phe  Leu  Leu  Arg  Leu  Ser  Lys  Leu
                         290                            295                             300
Thr  Lys  Glu  Asp  Glu  Gln  Gln  Gln  Ala  Leu  Gln  Asp  Ile  Ala  Ser
                         305                            310                             315
Arg  Cys  Thr  Ala  Asn  Asp  Leu  Lys  Cys  Ile  Ile  Arg  Leu  Ile  Lys
                         320                            325                             330
His  Asp  Leu  Lys  Met  Asn  Ser  Gly  Ala  Lys  His  Val  Leu  Asp  Ala
                         335                            340                             345
Leu  Asp  Pro  Asn  Ala  Tyr  Glu  Ala  Phe  Lys  Ala  Ser  Arg  Asn  Leu
                         350                            355                             360
Gln  Asp  Val  Val  Glu  Arg  Val  Leu  His  Asn  Ala  Gln  Glu  Val  Glu
                         365                            370                             375
Lys  Glu  Pro  Gly  Gln  Arg  Arg  Ala  Leu  Ser  Val  Gln  Ala  Ser  Leu
                         380                            385                             390
Met  Thr  Pro  Val  Gln  Pro  Met  Leu  Ala  Glu  Ala  Cys  Lys  Ser  Val
                         395                            400                             405
Glu  Tyr  Ala  Met  Lys  Lys  Cys  Pro  Asn  Gly  Met  Phe  Ser  Glu  Ile
                         410                            415                             420
Lys  Tyr  Asp  Gly  Glu  Arg  Val  Gln  Val  His  Lys  Asn  Gly  Asp  His
                         425                            430                             435
Phe  Ser  Tyr  Phe  Ser  Arg  Ser  Leu  Lys  Pro  Val  Leu  Pro  His  Lys
                         440                            445                             450
Val  Ala  His  Phe  Lys  Asp  Tyr  Ile  Pro  Gln  Ala  Phe  Pro  Gly  Gly
                         455                            460                             465
His  Ser  Met  Ile  Leu  Asp  Ser  Glu  Val  Leu  Leu  Ile  Asp  Asn  Lys
                         470                            475                             480
Thr  Gly  Lys  Pro  Leu  Pro  Phe  Gly  Thr  Leu  Gly  Val  His  Lys  Lys
                         485                            490                             495
Ala  Ala  Phe  Gln  Asp  Ala  Asn  Val  Cys  Leu  Phe  Val  Phe  Asp  Cys
                         500                            505                             510
Ile  Tyr  Phe  Asn  Asp  Val  Ser  Leu  Met  Asp  Arg  Pro  Leu  Cys  Glu
                         515                            520                             525
Arg  Arg  Lys  Phe  Leu  His  Asp  Asn  Met  Val  Glu  Ile  Pro  Asn  Arg
                         530                            535                             540
Ile  Met  Phe  Ser  Glu  Met  Lys  Arg  Val  Thr  Lys  Ala  Leu  Asp  Leu
                         545                            550                             555
Ala  Asp  Met  Ile  Thr  Arg  Val  Ile  Gln  Glu  Gly  Leu  Glu  Gly  Leu
                         560                            565                             570
Val  Leu  Lys  Asp  Val  Lys  Gly  Thr  Tyr  Glu  Pro  Gly  Lys  Arg  His
                         575                            580                             585
```

| Trp | Leu | Lys | Val | Lys<br>590 | Lys | Asp | Tyr | Leu | Asn<br>595 | Glu | Gly | Ala | Met | Ala<br>600 |
| Asp | Thr | Ala | Asp | Leu<br>605 | Val | Val | Leu | Gly | Ala<br>610 | Phe | Tyr | Gly | Gln | Gly<br>615 |
| Ser | Lys | Gly | Gly | Met<br>620 | Met | Ser | Ile | Phe | Leu<br>625 | Met | Gly | Cys | Tyr | Asp<br>630 |
| Pro | Gly | Ser | Gln | Lys<br>635 | Trp | Cys | Thr | Val | Thr<br>640 | Lys | Cys | Ala | Gly | Gly<br>645 |
| His | Asp | Asp | Ala | Thr<br>650 | Leu | Ala | Arg | Leu | Gln<br>655 | Asn | Glu | Leu | Asp | Met<br>660 |
| Val | Lys | Ile | Ser | Lys<br>665 | Asp | Pro | Ser | Lys | Ile<br>670 | Pro | Ser | Trp | Leu | Lys<br>675 |
| Val | Asn | Lys | Ile | Tyr<br>680 | Tyr | Pro | Asp | Phe | Ile<br>685 | Val | Pro | Asp | Pro | Lys<br>690 |
| Lys | Ala | Ala | Val | Trp<br>695 | Glu | Ile | Thr | Gly | Ala<br>700 | Glu | Phe | Ser | Lys | Ser<br>705 |
| Glu | Ala | His | Thr | Ala<br>710 | Asp | Gly | Ile | Ser | Ile<br>715 | Arg | Phe | Pro | Arg | Cys<br>720 |
| Thr | Arg | Ile | Arg | Asp<br>725 | Asp | Lys | Asp | Trp | Lys<br>730 | Ser | Ala | Thr | Asn | Leu<br>735 |
| Pro | Gln | Leu | Lys | Glu<br>740 | Leu | Tyr | Gln | Leu | Ser<br>745 | Lys | Glu | Lys | Ala | Asp<br>750 |
| Phe | Thr | Val | Val | Ala<br>755 | Gly | Asp | Glu | Gly | Ser<br>760 | Ser | Thr | Thr | Gly | Gly<br>765 |
| Ser | Ser | Glu | Glu | Asn<br>770 | Lys | Gly | Pro | Ser | Gly<br>775 | Ser | Ala | Val | Ser | Arg<br>780 |
| Lys | Ala | Pro | Ser | Lys<br>785 | Pro | Ser | Ala | Ser | Thr<br>790 | Lys | Lys | Ala | Glu | Gly<br>795 |
| Lys | Leu | Ser | Asn | Ser<br>800 | Asn | Ser | Lys | Asp | Gly<br>805 | Asn | Met | Gln | Thr | Ala<br>810 |
| Lys | Pro | Ser | Ala | Met<br>815 | Lys | Val | Gly | Glu | Lys<br>820 | Leu | Ala | Thr | Lys | Ser<br>825 |
| Ser | Pro | Val | Lys | Val<br>830 | Gly | Glu | Lys | Arg | Lys<br>835 | Ala | Ala | Asp | Glu | Thr<br>840 |
| Leu | Cys | Gln | Thr | Lys<br>845 | Val | Leu | Leu | Asp | Ile<br>850 | Phe | Thr | Gly | Val | Arg<br>855 |
| Leu | Tyr | Leu | Pro | Pro<br>860 | Ser | Thr | Pro | Asp | Phe<br>865 | Ser | Arg | Leu | Arg | Arg<br>870 |
| Tyr | Phe | Val | Ala | Phe<br>875 | Asp | Gly | Asp | Leu | Val<br>880 | Gln | Glu | Phe | Asp | Met<br>885 |
| Thr | Ser | Ala | Thr | His<br>890 | Val | Leu | Gly | Ser | Arg<br>895 | Asp | Lys | Asn | Pro | Ala<br>900 |
| Ala | Gln | Gln | Val | Ser<br>905 | Pro | Glu | Trp | Ile | Trp<br>910 | Ala | Cys | Ile | Arg | Lys<br>915 |
| Arg | Arg | Leu | Val | Ala<br>920 | Pro | Cys | | | | | | | | |

( 2 ) INFORMATION FOR SEQ ID NO:3:

( i ) SEQUENCE CHARACTERISTICS:
        ( A ) LENGTH: 29 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

CGCGGATCCA TGGCTGAGCA ACGGTTCTG 29

( 2 ) INFORMATION FOR SEQ ID NO:4:

( i ) SEQUENCE CHARACTERISTICS:
        ( A ) LENGTH: 27 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

GCGTCTAGAC TAGCAGGGAG CTACCAG 27

( 2 ) INFORMATION FOR SEQ ID NO:5:

( i ) SEQUENCE CHARACTERISTICS:
        ( A ) LENGTH: 29 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:5:

CGCGAATCCA TGGCTGAGCA ACGGTTCTG 29

( 2 ) INFORMATION FOR SEQ ID NO:6:

( i ) SEQUENCE CHARACTERISTICS:
        ( A ) LENGTH: 27 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:6:

GCGTCTAGAC TAGCAGGGAG CTACCAG 27

( 2 ) INFORMATION FOR SEQ ID NO:7:

( i ) SEQUENCE CHARACTERISTICS:
        ( A ) LENGTH: 29 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:7:

CGCGAATCCA TGGCTGAGCA ACGGTTCTG 29

( 2 ) INFORMATION FOR SEQ ID NO:8:

( i ) SEQUENCE CHARACTERISTICS:
        ( A ) LENGTH: 56 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:8:

GCGTCTAGAT CAAGCGTAGT CTGGGACGTC GTATGGGTAG CAGGGAGCTA CCAGTC 56

(2) INFORMATION FOR SEQ ID NO:9:

(i) SEQUENCE CHARACTERISTICS:
        (A) LENGTH: 21 AMINO ACIDS
        (B) TYPE: AMINO ACID
        (C) STRANDEDNESS:
        (D) TOPOLOGY: LINEAR (ii) MOLECULE TYPE: PEPTIDE (xi) SEQUENCE DESCRIPTION: SEQ ID NO:9:

```
Lys Cys Pro Asn Gly Met Phe Ser Glu Ile Lys Tyr Asp Gly Glu
                  5                  10                  15  Arg
Val Gln Val His Lys
            20
```